(12) United States Patent
Phillips et al.

(10) Patent No.: US 10,335,520 B2
(45) Date of Patent: Jul. 2, 2019

(54) DEVICE AND METHOD FOR CLEARING TUBING

(71) Applicants: Janet L. F. Phillips, Oconomowoc, WI (US); Michael J. Phillips, New Bern, NC (US); VECTOR SURGICAL, LLC, Waukesha, WI (US)

(72) Inventors: Janet L. F. Phillips, Oconomowoc, WI (US); Michael J. Phillips, New Bern, NC (US); Glenn Walters, Port Washington, WI (US)

(73) Assignee: VECTOR SURGICAL, LLC, Waukesha, WI (US)

( * ) Notice: Subject to any disclaimer, the term of this patent is extended or adjusted under 35 U.S.C. 154(b) by 118 days.

(21) Appl. No.: 15/313,320

(22) PCT Filed: Apr. 28, 2016

(86) PCT No.: PCT/US2016/029759
§ 371 (c)(1),
(2) Date: Nov. 22, 2016

(87) PCT Pub. No.: WO2016/176433
PCT Pub. Date: Nov. 3, 2016

(65) Prior Publication Data
US 2017/0203019 A1    Jul. 20, 2017

Related U.S. Application Data

(60) Provisional application No. 62/153,770, filed on Apr. 28, 2015.

(51) Int. Cl.
*A61M 1/00* (2006.01)
*A61J 15/00* (2006.01)

(52) U.S. Cl.
CPC ........ *A61M 1/0078* (2013.01); *A61J 15/0076* (2015.05); *A61M 2205/8206* (2013.01); *A61M 2209/10* (2013.01)

(58) Field of Classification Search
CPC ........ A61M 1/0078; A61M 2205/8206; A61M 2209/10; A61J 15/0076
See application file for complete search history.

(56) References Cited

U.S. PATENT DOCUMENTS

| 2,197,310 A | 4/1940 | Lincoln |
| 7,309,055 B1 | 12/2007 | Spiegel et al. |

(Continued)

FOREIGN PATENT DOCUMENTS

| CH | 278763 A | 10/1951 |
| DE | 29713696 U1 | 9/1997 |

OTHER PUBLICATIONS

International Search Report and Written Opinion, issued by the ISA/US Receiving Office, regarding corresponding international patent application Serial No. PCT/US2016/029759; dated Sep. 30, 2016, 12 pages.

(Continued)

*Primary Examiner* — Bradley J Osinski
(74) *Attorney, Agent, or Firm* — Fox Rothschild LLP

(57) ABSTRACT

A device for moving contents of a tube by acting on the exterior of the tube is provided. The device includes a housing having a top portion and a bottom portion, the top portion including a tube passageway extending along a length thereof for holding a tube therein. A roller housed within a roller chassis contacts the tube and is configured to move between a first position in which the tube is disengaged and a second position in which the tube is engaged. A second roller is rotatably coupled to an actuator for rotatably energizing the second roller and is moveable between a first position in which the tube is disengaged and (Continued)

a second position in which the tube is engaged. A lever is operably coupled to the housing and configured to actuate a motor to move the second roller to the second position. The first roller and the second roller are configured to compress the tube to move contents within the tube.

22 Claims, 15 Drawing Sheets

(56) References Cited

U.S. PATENT DOCUMENTS

| 2004/0102716 | A1 | 5/2004 | Mobbs et al. |
| 2006/0081647 | A1 | 4/2006 | Wilson et al. |
| 2009/0120957 | A1 | 5/2009 | Phillips |
| 2010/0294378 | A1 | 11/2010 | Kleimann, Sr. |

OTHER PUBLICATIONS

Extended European Search Report, issued by the European Patent Office, regarding corresponding patent application Serial No. EP 16787137.5; dated Nov. 19, 2018; 7 pages.

DEVICE AND METHOD FOR CLEARING TUBING

CROSS REFERENCE TO RELATED APPLICATIONS

This application is a national stage patent application of International patent application Serial No.: PCT/US2016/029759, filed on Apr. 28, 2016; which claims the benefit of U.S. Provisional patent application Serial No.: 62/153770, filed on Apr. 28, 2015; the entireties of which are hereby incorporated by reference.

FIELD OF THE INVENTION

The present invention relates generally to a device for clearing or stripping debris and other matter from a flexible tube. In particular the invention relates to a device that is easily usable by a patient to clear a surgical drain or move contents through a feeding tube.

BACKGROUND OF THE INVENTION

Tubing is used in many medical procedures in particular surgical drains and feeding tubes. Surgical drains are used following a wide variety of invasive surgeries to allow for drainage of matter and/or debris from the surgical area. Representative surgeries include breast surgery, cosmetic surgery, orthopedic surgery, radical neck procedures, thyroidectomy surgery, cardiothoracic surgery and general surgery. The fluid build-up may cause swelling and pooling of blood and fluid resulting in discomfort to patient, or may lead to infection and may delay or prevent healing of the surgical site. Consequently, a surgical drain, typically a flexible tube, is placed with one end in the surgical site and the other end outside of the patient and may stay in place for one to three weeks after surgery. The matter and/or debris being drained includes mostly viscous fluids such as pus, serum and blood, etc. but may also include some solid or semi-solid matter such as clots and other debris which may solidify within the tube thereby blocking flow from the drain. Feeding tubes are used to deliver food when the patient is unable to eat normally by mouth, is unable to swallow safely, or needs nutritional supplementation. Over time the feeding tube may tend to clog with debris of coagulated food particles.

To prevent the blockages before they form or clear them after they form, the surgical drain tube or feeding tube may need to be changed or cleared. For surgical drains, the standard process for clearing or "unclogging" the drains, or maintaining "drain patency," is to instruct the patient to "milk" the drain, which means to squeeze the drain between two fingers and in so doing, pull the matter down the drain away from the body. However, there are several problems with this method. First, it is uncomfortable at the surgical site, where the drain is sutured to skin, for the patient who is still recovering from surgery. Also, it may be difficult physically to perform the task if the patient has arthritis which affects their ability to grip the drain, or if the drain is located in an area that is difficult for the patient to reach. In addition, it is time consuming especially if several drains need to be cleared. Further, patients do not do it effectively or they do not do it with the frequency instructed because they are concerned with dislodging the drain from the surgical site. Moreover, the constant pulling of the flexible tubing stretches it, resulting in an unnecessarily long and inconvenient length or the need for replacement. For feeding tubes, patients are often instructed to "milk" the drain from the exterior to help release clogs or blockages of material inside the tube. This is problematic for several of the same reasons cited above, such as ineffectiveness of the procedure, lack of patient compliance, and stretching of the tube. A blocked feeding tube may require the patient to undergo an additional surgical procedure to replace the tube, resulting in further burden to the patient as well as additional costs.

Commercially available devices have attempted to deal with the foregoing problems. However, they are awkward to use, less appealing to the patient and their relative effectiveness is yet untested.

Accordingly, there is a need for a device and method for clearing drains that: effectively moves the contents of the tube or drain through from the exterior, requires very little dexterity and/or effort by the patient, expedites movement of the tube through the device as it performs the clearing function, does not stretch the tube, minimizes the risk of pulling the surgical drain out of the surgical site, can be used by one hand, can be sterilized using gamma radiation, is cost effective, and can reliably solve the aforementioned problems.

BRIEF SUMMARY OF THE INVENTION

The problems outlined above are addressed by the device and method for moving the contents of a surgical drain or feeding tube by acting on the exterior of the tubing in accordance with the invention.

According to one aspect of the invention, the device provides a more effective way to keep surgical drains clear and promotes fewer seromas, faster healing, less risk of infection from repeated aspirations and fewer delays of adjuvant therapy.

In another aspect of the invention the device for moving the contents of a tubing by acting on the exterior of the tubing includes a housing including a top portion and a bottom portion, said top portion including a tube passageway extending along a length thereof for holding a tube therein; a first roller including a pair of lips that define a first channel therebetween and a second roller including a pair of lips that define a second channel therebetween, said first and second rollers configured to compress said tube by a predetermined amount; first and second roller chassis operably coupled to the housing for mounting said first and second roller therein, said first and second roller chassis pivotal between a first position in which the tube is disengaged and a second position in which the tube is engaged; a motor for energizing at least said first roller; and at least one lever operably coupled to said housing for actuating said motor.

In another aspect of the invention, the first roller channel is convex and the second roller channel is concave.

In another aspect of the invention, the device includes a spring for biasing the roller chassis in the first position. The spring may be a leaf spring or may be a compression spring.

In another aspect of the invention, the device includes first and second levers mounted to said housing at a single pivot point.

In another aspect of the invention, the motor energizes both the first and second rollers.

In another aspect of the invention a device for moving contents of a tube by acting on the exterior of the tube is provided. The device includes a housing including a top portion and a bottom portion, the top portion including a tube passageway extending along a length thereof for holding the tube therein; a first roller and a second roller moveable between a first position and a second position and configured to compress the tube in the second position; a first roller chassis coupled to the housing for mounting the first roller therein and a second roller chassis coupled to the housing for mounting the second roller therein, the first and second roller chasses moveable between a first position in which the tube is disengaged and a second position in which the tube is engaged; a motor for energizing at least the first roller; and at least one lever operably coupled to the housing for actuating the motor.

In another aspect of the invention the device for moving the contents of a tubing by acting on the exterior of the tubing includes a housing including a top portion and a bottom portion, said top portion including a tube passageway extending along a length thereof for holding a tube therein; a first roller including a pair of lips that form a first channel therebetween and a second roller including a pair of lips that form a second channel therebetween, said first and second rollers configured to compress said tube by a pre-determined amount; a roller chassis for mounting said first and second roller therein, said roller chassis pivotal between a first position in which the tube is disengaged and a second position in which the tube is engaged; and at least one lever operably coupled to said housing for causing said first and/or second roller to pivot and engage tubing positioned within said passageway.

In yet another aspect of the invention the device for moving the contents of a tubing by acting on the exterior of the tubing includes a housing having a top portion and a bottom portion, the top portion including a tube passageway extending along a length thereof for holding a tube therein; a roller chassis moveable between a first position and a second position and coupled to the housing; a first roller for contacting the tube, the first roller housed within the roller chassis and moveable between a first position in which the tube is disengaged and a second position in which the tube is engaged; a second roller rotatably coupled to an actuator for rotatably energizing the second roller, the second roller moveable between a first position in which the tube is disengaged and a second position in which the tube is engaged, the first roller and the second roller configured to compress the tube; biasing means for biasing the first roller and the second roller in opposite directions; and at least a first lever operably coupled to the housing, the first lever configured to actuate the actuator and move the second roller to the second position.

In a further aspect of the invention the device for moving contents of a tubing by acting on the exterior of the tubing includes a housing including a top portion and a bottom portion, the top portion including a tube passageway extending along a length thereof for holding a tube therein; a roller chassis moveable between a first position and a second position slidably coupled to the housing the roller chassis including first and second compartments; a first roller including a pair of lips that form a passageway therebetween for contacting the tube, the first roller housed within the roller chassis in the first roller chassis compartment and moveable between a first position in which the tube is disengaged and a second position in which the tube is engaged; a second roller rotatably coupled to an actuator for rotatably energizing the second roller, the second roller moveable between a first pivot position in which the tube is disengaged and a second pivot position in which the tube is engaged, the first roller and the second roller configured to compress the tube by a pre-determined amount; biasing means for biasing the first roller and the second roller in opposite directions; and at least a first lever operably coupled to the housing, the first lever configured to actuate the actuator and move the second roller to the second pivot position.

In yet a further aspect of the invention a device for moving contents of a tube by acting on the exterior of the tube includes a housing having a top portion and a bottom portion, the top portion including a tube passageway extending along a length thereof for holding the tube therein; a first roller including a pair of lips that define a first channel therebetween and a second roller including a pair of lips that define a second channel therebetween, the first and second rollers configured to compress the tube by an amount sufficient to move the contents contained therein; first and second roller chassis operably coupled to the housing for mounting the first and second roller therein, the first and second roller chassis pivotal between a first position in which the tube is disengaged and a second position in which the tube is engaged; and at least one lever operably coupled to the housing for causing the first or second roller to pivot and engage the tube positioned within the passageway.

BRIEF DESCRIPTION OF THE DRAWINGS

For a better understanding of the invention, and to show how the same may be carried into effect, reference will now be made, by way of example, to the accompanying figures, in which.

DETAILED DESCRIPTION OF THE INVENTION

Figure 3:
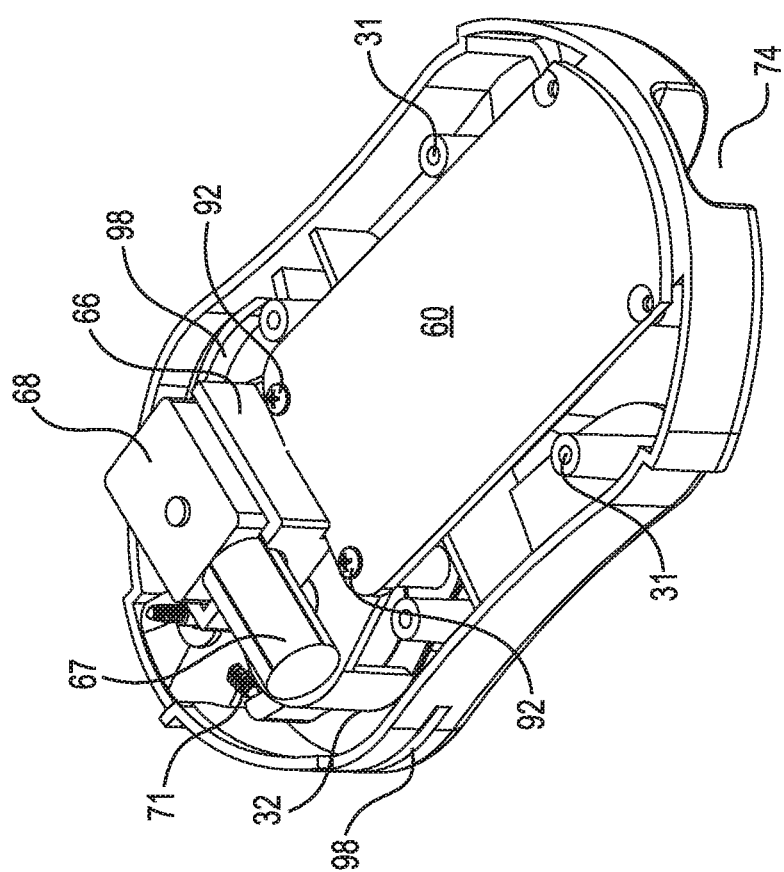
FIG. 3 is a perspective view of the drain clearing device of FIG. 2 showing a plate securing the roller chaises.

Referring now to FIGS. 1 through 6 the drain clearing device 10 in accordance with the invention is shown. The drain clearing device 10 includes housing 12 having a top clamshell 14 and a bottom clamshell 16 configured to be fastened together by adhesive, snap fit or threaded fastener or other means known to those of skill in the art. Top clamshell 14 includes first and second levers 18, 20 pivotally coupled at a single pivot point 26 by screw 100 to top clamshell 14 by first 28 and second 28' (as best seen in FIG. 3) pivot arms. First and second levers 18, 20 include a stop (not shown) thereon that stops the levers from being depressed further when the stop engages or abuts a corresponding piece in housing 12. First and second levers 18, 20 also include first projection and second projection 30, which are received by corresponding openings 98 in top clamshell 14. In operation first and second projections 30 engage roller chaises 32, 34 at a back portion thereof and push the roller chaises 32, 34 toward the center. Those of skill in the art will also appreciate that levers 18, 20 may include a flat outer surface 80, which allows the device to be marked on one or both levers with a logo or the contact information of the patient's hospital, physician, or clinic.

Top and bottom clamshells 14, 16 may advantageously each be integrally formed by injection molding. A variety of posts 31 (best seen in FIG. 2) may be formed within the top clamshell 14 during the injection molding process. Any suitable material, or combination of materials, can be selected for forming the various components of the apparatus of the present invention. Those of skill in the art will appreciate that materials are selected to have durability and rigidity sufficient for a desired application of the device and many plastic materials will meet these criteria. Also, for many medical applications, materials that are sterilizable, such as by gamma radiation, are also desirable. Accordingly, the unit may be supplied as a sterile unit or as a non-sterile unit. Top clamshell 14 may also advantageously be constructed of, or coated with, a lubricious material that facilitates ease of movement of the surgical drain tube 74 through passageway 78.

First and second levers 18, 20 are also each integrally formed, for example, by injection molding. The outer surface 88 of each lever 18, 20 may be concave which allows a user to easily and ergonomically hold the device 10 in either the left or right hand.

Roller chassis 32, 34 each include bottom 36 and top 38 portions and an approximately centrally-placed aperture 37 on the top and bottom portions 38, 36. Bottom portions 36 of first and second roller chasses also serve as mounting plates. Roller chasses 32, 34 also include a large aperture 33' on the front of the top portion 38 to enable roller chasses 32, 34 to be positioned on one or more of posts 31. Apertures 33 are located toward the front of the bottom portions 36 and receive retaining screws 90, 92. Central aperture 37 of the first roller chassis 32 receives pivot axel 35 about which first roller chassis 32 pivots in operation. Second roller chassis 34 includes a corresponding central aperture (not shown) which receives drive mechanism 69 which in turn is received by hole 43 in second roller 42. Second roller chassis 34 also includes clip 66 thereon for receiving motor 67 and gear housing 68.

Figure 1:
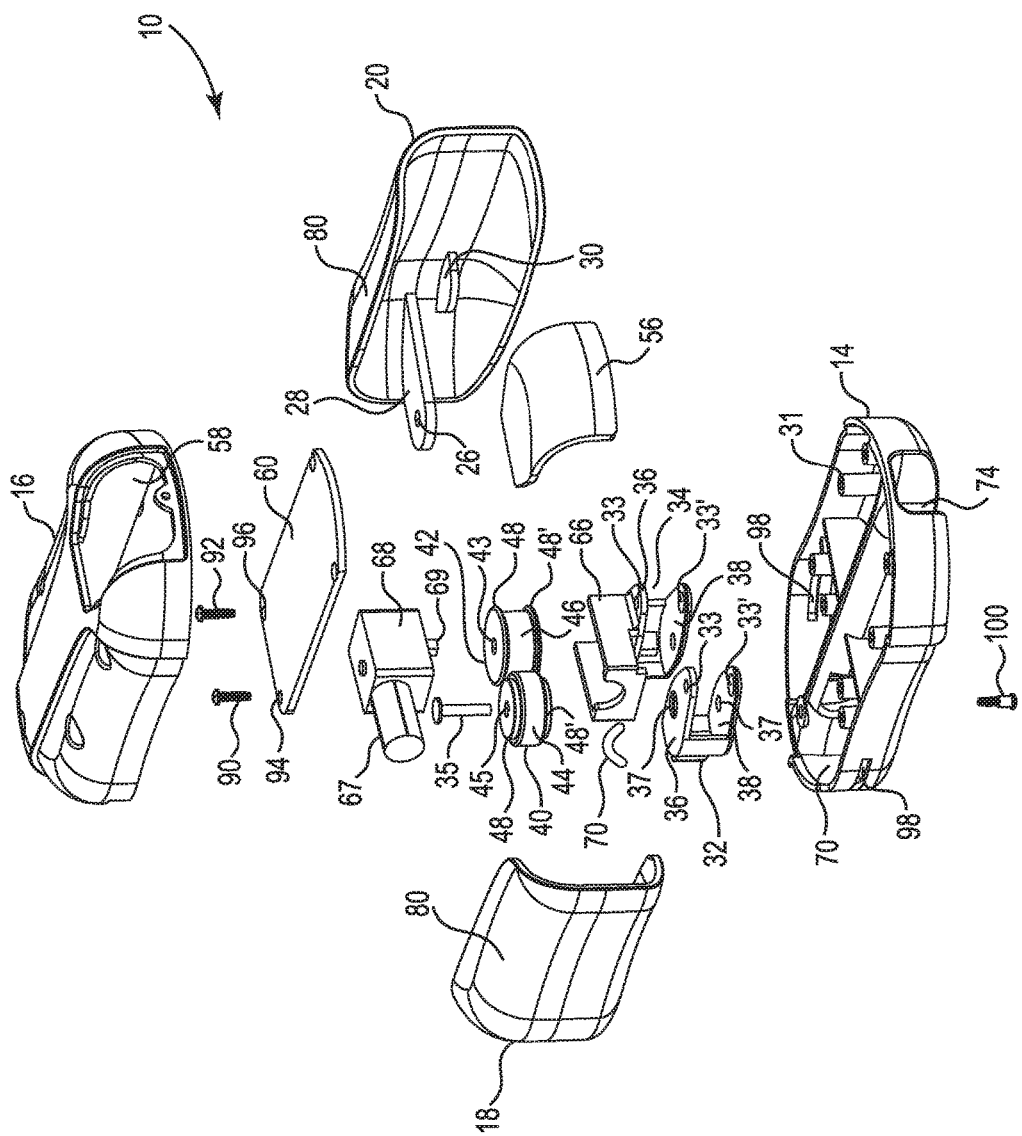
FIG. 1 is an exploded view of the drain clearing device in accordance with the invention oriented with the bottom clamshell at the top and the top clamshell at the bottom.
Figure 2:
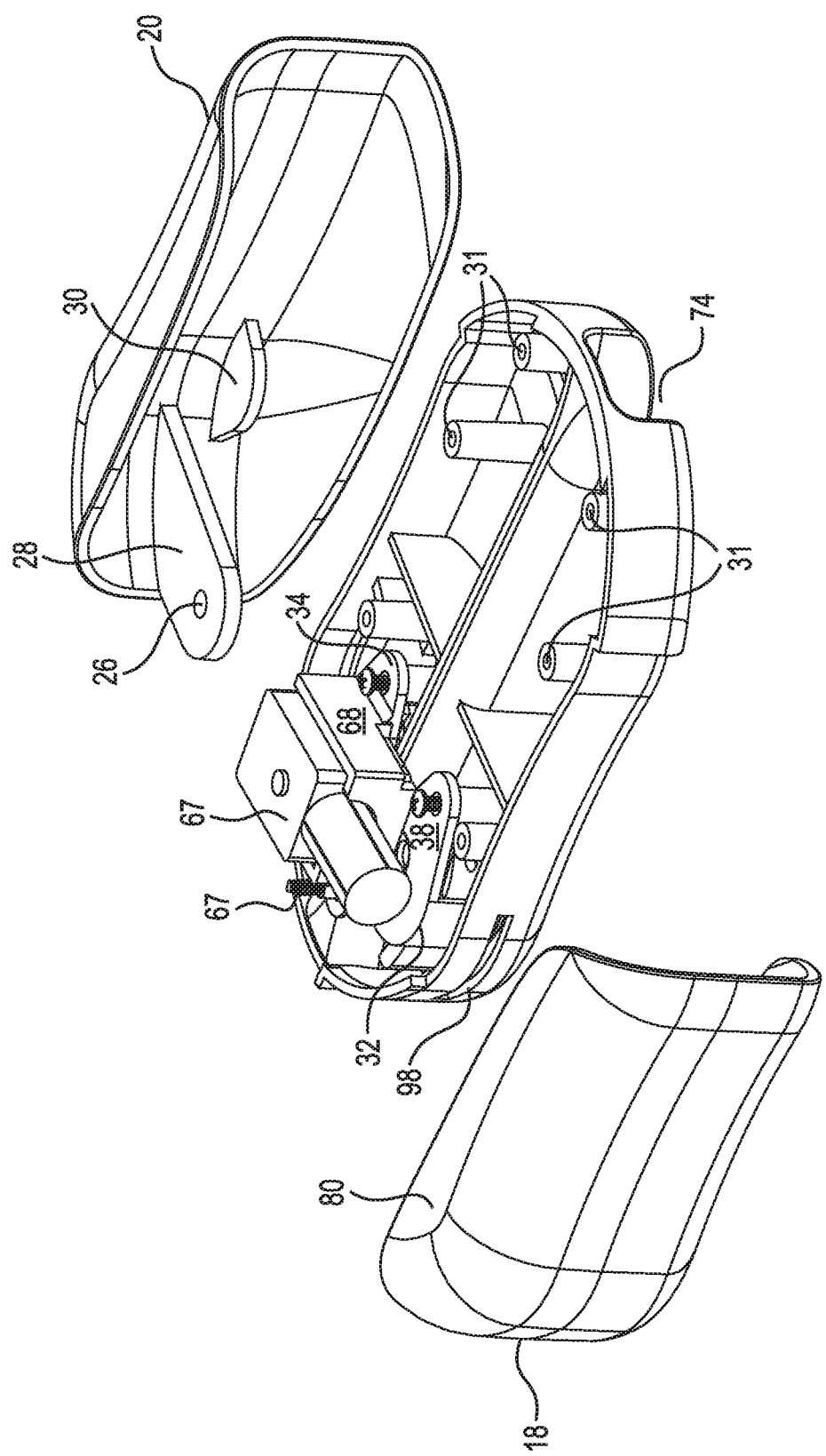
FIG. 2 is a perspective view of the drain clearing device in accordance with the invention with the bottom clamshell removed.

First and second rollers 40, 42 are rotatably received between top 38 and bottom 36 portions of first and second chassis 32, 34, respectively. Second roller 42 may optionally include top and bottom lips 48, 48' thereon. Those of skill in the art will appreciate that, if included, lips 48, 48' define a channel 46 therebetween designed to advantageously retain the drain tube 78 therein when in use. As depicted in FIG. 1 first roller 40 may also include lips 48, 48' and convex projection 44. Convex projection 44 is designed to mate with channel 46 in use. Thus, when the tubing 78 is placed therein and the device is actuated, as discussed in detail below, the mating of the two rollers acts to firmly compress the drain tube. Alternatively, the convex projection 44 of first roller 40 may be eliminated and lips 48, 48' and concave channel 46 are present in both rollers 40, 42. Still alternatively, "first" and "second" roller configurations may be reversed as "first" and "second" are relative terms. Rollers 40, 42 may be configured to close to a pre-determined gap such that channel 46 and convex projection 44 (or two channels 44 on rollers 40, 42 or, alternatively, two convex projections 44 on rollers 40, 42) consistently compress tubing 78 to allow clearing of the tubing 78. However, those of skill in the art will appreciate that a pre-determined gap is not necessary for the device to function. Rather, the device may include multiple settings (such as a mechanical or electrical switch moveably operable between a series of increasing numbers, e.g. 1-5) to provide the ideal gap between rollers for different tube sizes.

Figure 5:
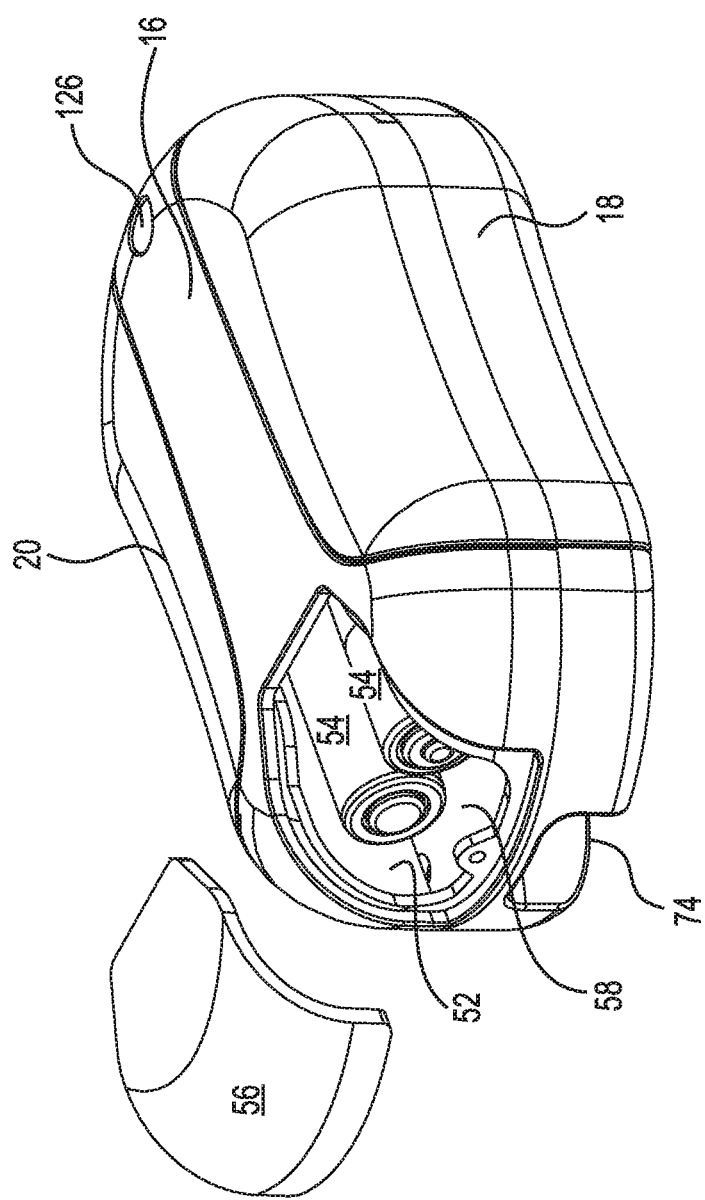
FIG. 5 is a perspective view of the drain clearing device in accordance with the invention showing a pivoting battery door at one end thereof and showing the pivot point of the two levers and single fastener at a second end thereof

As best seen in FIG. 5, bottom clamshell 16 includes an integrally molded battery compartment 52 that houses batteries 54. Battery compartment door 56 may pivotally attach to bottom clamshell 16. In use a user pivots the battery compartment door open to change the batteries by sliding them into the compartment. Those of skill in the art will appreciate that mountings other than a pivot mount are possible and fall within the scope of the invention. In addition, the battery door 56 may be pivotally mounted at the bottom of the compartment opening 58 and/or mounted so that the batteries may be dropping in from the top clamshell 14.

As best seen in FIG. 3, plate 60 encloses battery compartment 52. Plate 60 includes at least two holes 94, 96 thereon for receiving retaining pins 90, 92 which are also received by apertures 33, 33' and posts 31 to retain roller chassis 32, 34 in place. Apertures 33' of top portions 38 also serve as pivot points for first and second chasses 32, 34 to pivotally move from a first disengaged position to a second engaged position.

Clip 66 may be fixedly coupled and/or integrally molded with roller chassis 34 and operably retains motor and gear housing 68 which houses motor (not shown). Roller chassis mounting plate 38 also mounts to motor and gear housing 68 to prevent the motor from rotating when actuated. Those of skill in the art will appreciate that the device may also include a mechanical, electrical or electro-mechanical on/off switch that actuates the motor.

Leaf spring 70 operably mounted in bottom clamshell 16 acts to bias at least one of first mounting element and second mounting element in the "disengaged" position in which the surgical drain tubing 78 is not engaged. Alternatively, the device may include two leaf springs 70 mounted on opposing sides of the bottom clamshell for biasing both first and second chasses 32, 34 in the "disengaged" position. Still alternatively, a compression spring 71 may be substituted as best seen in FIG. 3. When assembled, lever pivot arms 28, 30 overlap and attach to bottom clamshell 16 via single pivot point 26.

Figure 4:
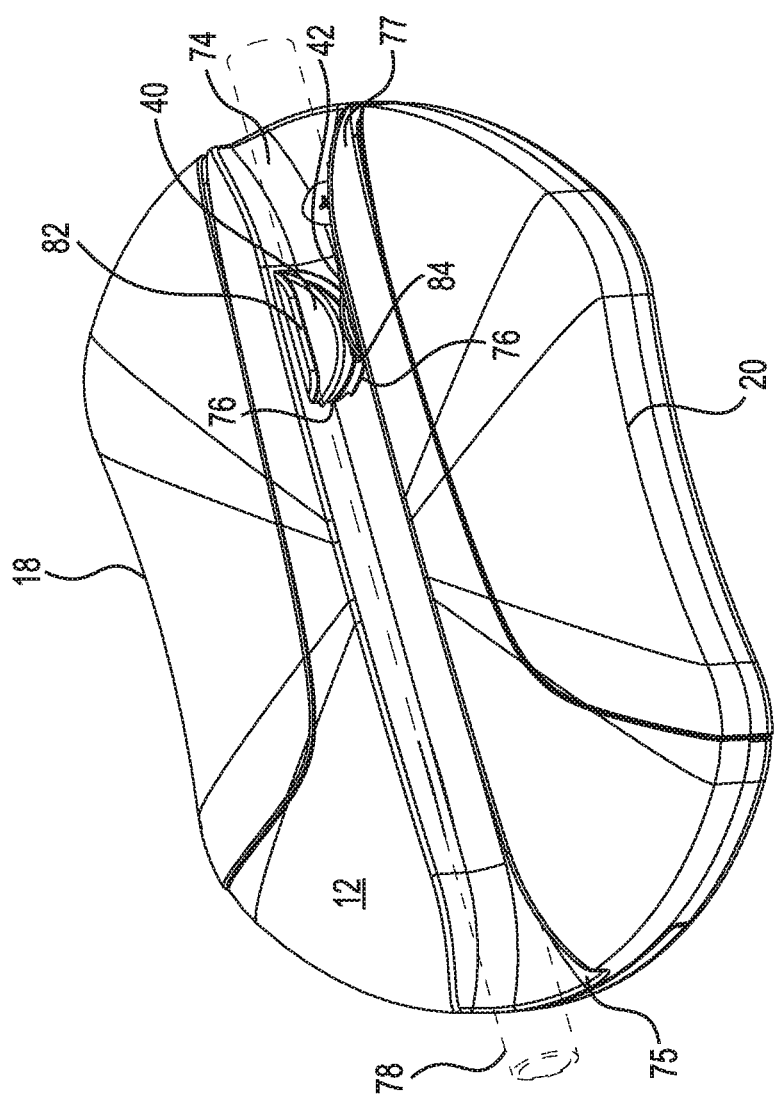
FIG. 4 is a perspective view of the drain clearing device in accordance with the invention showing two side levers, tube passageway and tube guide.

Top clamshell 12 includes an integrally molded passageway or groove 74 thereon which accommodates drain tubing 78 therein during operation. As best seen in FIG. 4 top clamshell 14 also includes corresponding windows 76 through which rollers 40, 42 project into passageway 74 in operation. The distal and proximal ends of 75, 77 of passageway 74 may be fan-shaped and thus have a width that is greater than the width of the passageway 74 in the center. Proximal ends 75, 77 allow the surgical drain tubing 78 (or feeding tube) to be easily inserted and removed from passageway 74 as well as facilitate movement of the tube through the device when tubing enters or exits the device at multiple angles. Other shapes may be used and fall within the scope of the invention. Top clamshell 14 may also include opposing strips of flexible or pliable material 82, 84, as best seen in FIG. 4, such as silicone or rubber and the like, that acts as a tube guide and also assists in holding the surgical tubing in place during operation. Those of skill in the art will appreciate that one tube guide (82 or 84) may be utilized and that if two tube guides 82, 84 are used they may not necessarily have to be directly opposing each other but may also be offset from one another. Those of skill in the art will also appreciate that tube guides 82, 84 are ideally pliable to allow for easy insertion of flexible tubing 78 into passageway 74. Those of skill in the art will appreciate that tube guides 82, 84 may be operably coupled to the top portions 38 of one or both roller chasses 32, 34 as depicted in FIGS. 7-12. Those of skill in the art will also appreciate that the width of the passageway may be varied depending on the outer diameter of the surgical drain or feeding tube tubing to be inserted therein. However, for economies in the manufacturing process the passageway 74 should be sufficiently wide to accommodate most diameters of tubing, such as 15, 19, 20, 22 and/or 24 French surgical drains or slightly larger feeding tubes, as the tube guides 82, 84 that overlap each side of a portion of passageway 74, in addition to channel 46, will hold the tubing 78 in place.

In operation, a user places surgical tubing 78 in passageway 74 under the pliable tube guides 82, 84 (or a single tube guide). The user then squeezes levers 18, 20 toward housing 12. Lever 20 triggers a switching element (not shown) which actuates or energizes an actuator mechanism. Many different types of actuators may be used including, but not limited to, motors, rotary solenoids, electromechanical rotary devices, and electromagnetic rotary devices. As an exemplary embodiment, actuator is disclosed herein as a motor 67 and gear housing 68, which houses gears that rotate drive mechanism 69. When motor 67 is actuated, the drive mechanism causes roller 42 to rotatably move. Those of skill in the art will appreciate that the motor 67 may also actuate roller 40 thus actuating both rollers 40, 42 or alternatively the device could accommodate two motors that actuate one roller each.

At the same time, squeezing the levers 18, 20 causes projections 30 to press on the roller chassis 32, 34 (which in turn exerts a counterforce against the leaf spring 70 or compression spring 71) and the roller chasses 32, 34 pivot such that channel 46 and convex projection 44 engage tubing 78. Those of skill in the art will appreciate that either the upper and lower lips 48, 48' or the concave and convex mating relationship of the channel 46 and projection 46 would be alone sufficient to hold the tubing 74 in place. Thus, upper and lower lips 48, 48' on the first roller 40 may be eliminated and the convex portion alone would be sufficient to maintain the tubing 78 in place. Similarly, upper and lower lips 48, 48' may be eliminated entirely. Although the motorized roller 42 will cause the tubing 78 to move through the passageway 74, the user may also guide the device down the length of the tubing thus clearing it of its contents. The levers 18, 20 are also engageable with a dead-man's switch (not shown) such that as soon as a user releases one or both of the levers 18, 20 the motor becomes de-energized and roller 42 cease to rotates. Releasing levers 18, 20 also releases force on leaf springs 70 (or two leaf springs 70 or one or two compression springs 71) causing the roller chassis 32, 34 to pivot back to the original "disengaged" position.

Figure 6:
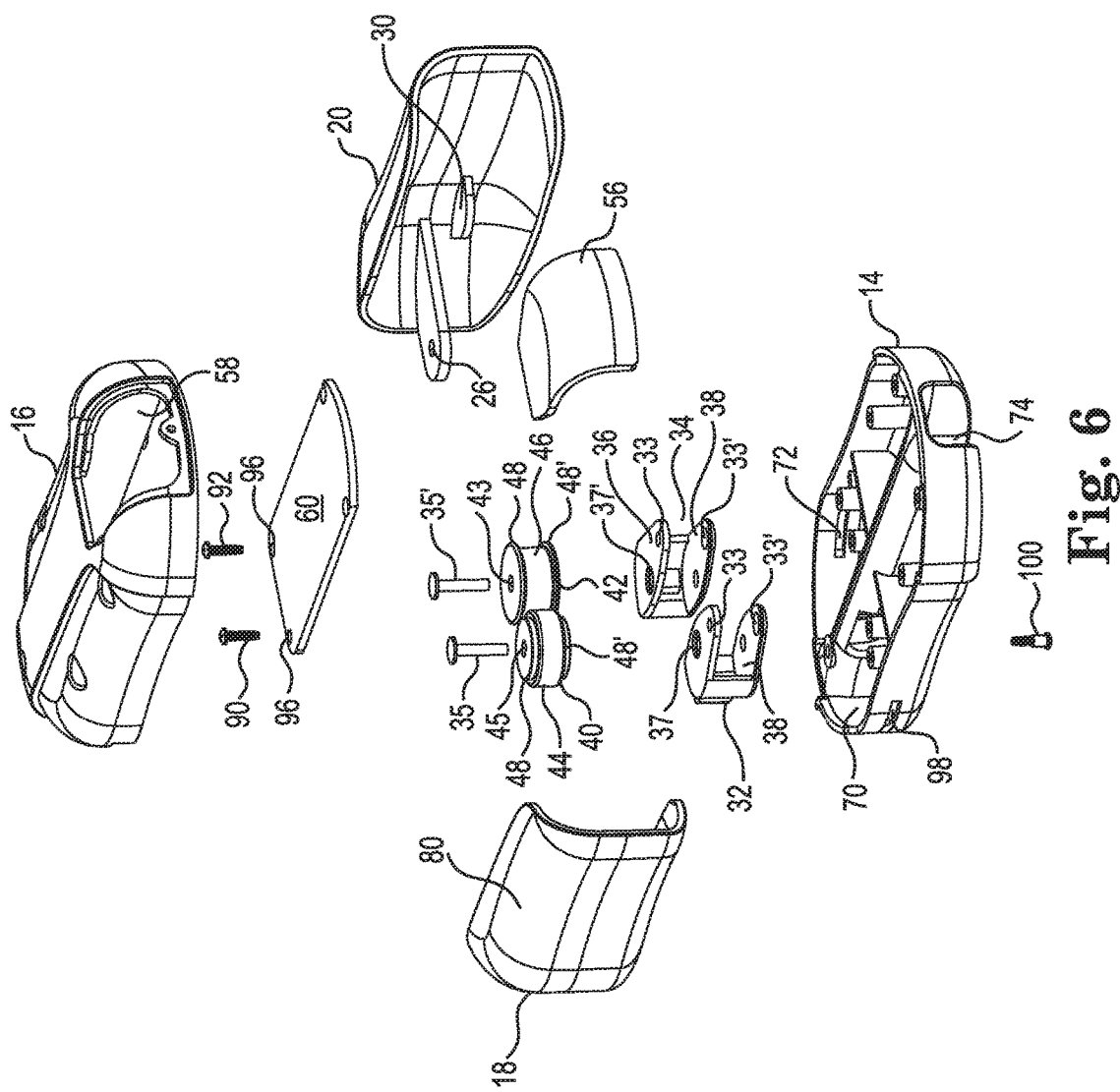
FIG. 6 is an exploded view of a non-motorized embodiment of the invention.
Figure 7:
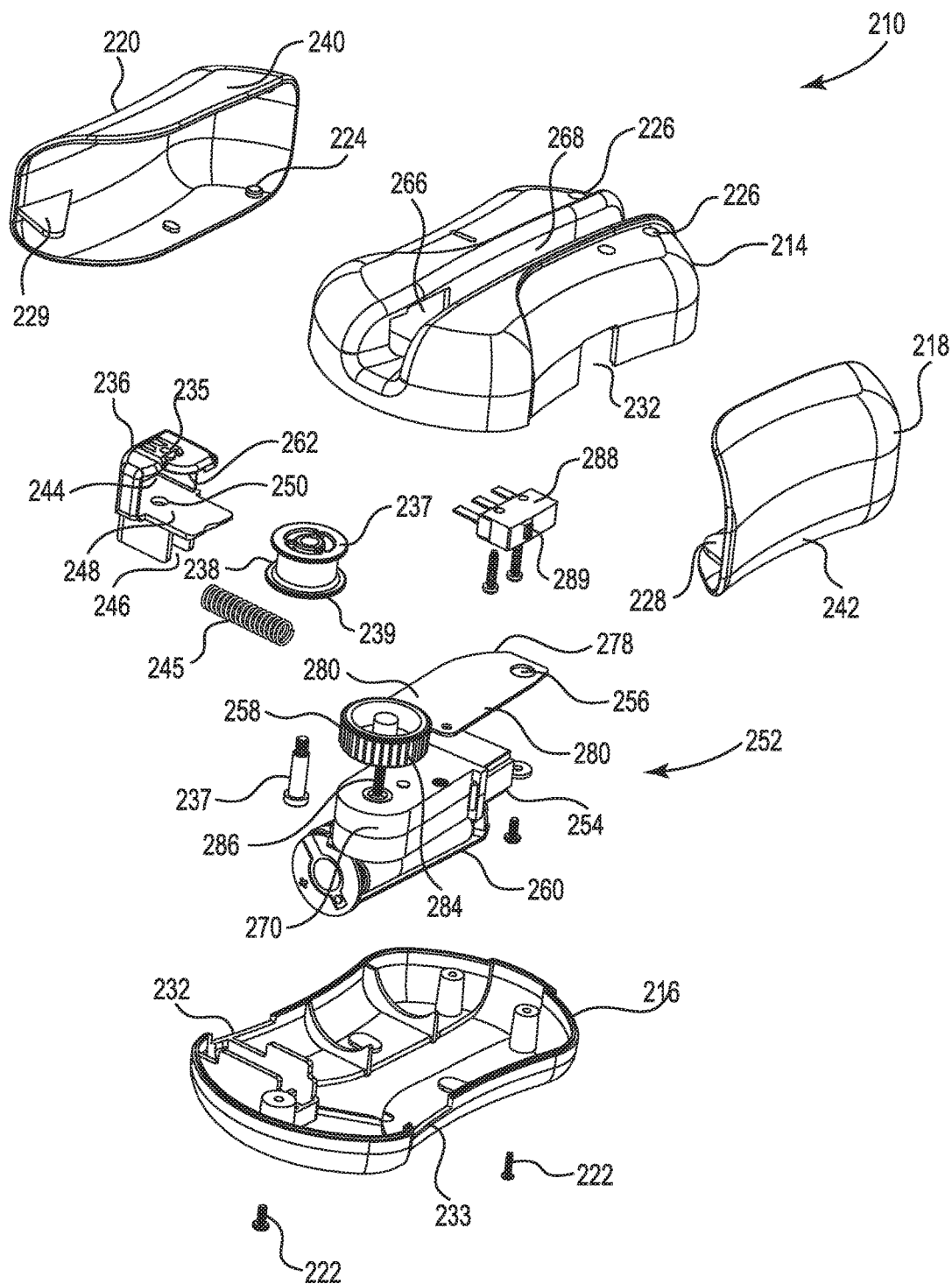
FIG. 7 is an exploded view of an alternative embodiment of the drain clearing device in accordance with the invention oriented with the top clamshell at the top and the bottom clamshell at the bottom.

Referring now to FIG. 6 a non-motorized embodiment of the invention is shown. As can be seen, clip 66 and motor 67 with gear box 68 have been eliminated. Like reference numerals correspond to like elements of FIGS. 1-5. The central apertures 37, 37' of the first and second roller chasses 35 receive pivot axels 35, 35' which in turn are received by holes 45, 43 in first 40 and second rollers 42. Those of skill in the art will appreciate, however, that it is not necessary for both roller chasses to pivot. Only one roller chassis may pivot and the device would still be functional. Those of skill in the art will also appreciate that either the upper and lower lips 48, 48' or the concave and convex mating relationship of the rollers 40, 42 would be alone sufficient to hold the tubing 74 in place. Thus, upper and lower lips 48, 48' on the first roller 40 may be eliminated and the convex portion alone would be sufficient to maintain the tubing 78 in place. Similarly, upper and lower lips 48, 48' may be eliminated entirely. In operation, a user places surgical tubing 78 in passageway 74 under the pliable tube guides 82, 84 although as discussed only one tube guide may be used. The user then squeezes levers 18, 20 toward housing 12. Squeezing the levers 18, 20 causes projections 30 to press on the roller chassis 32, 34 (which in turn exerts a counterforce against the leaf or compression springs) causing the roller chassis 32, 34 to pivot such that the concave and convex mating relationship of rollers 40, 42 apply force to the tubing 78. Keeping the levers 18, 20 squeezed, the user then guides the device down the length of the tubing thus clearing or stripping it of its contents. Releasing levers 18, 20 releases force on leaf springs 70, 72 causing the roller chassis 32, 34 to pivot back to their original "disengaged" position.

Referring now to FIGS. 7-12 an alternative embodiment of a tube clearing device in accordance with the invention is illustrated. Drain clearing device 210 broadly includes housing 212 having a top clamshell 214 and a bottom clamshell 216 configured to be fastened together by adhesive, snap fit or threaded fastener or other means known to those of skill in the art. As illustrated, the top and bottom clamshells are fastened together using a plurality of screws 222. Drain clearing device 210 includes first and second levers 218, 220 each of which has top and bottom pivot elements 224 pivotally coupled to top clamshell 214 and bottom clamshell 216 at points 226.

First lever 218 includes first projection 228 and third projection 230. Third projection 230 is received in opening 232 in housing 212 and contacts motor activation button 289 on switch 288. First projection 228 is received in opening 233 in housing 212 and contacts motor housing 270. Second lever 220 includes second projection 230 which is received by opening 234 in housing 212. Second projection 229 contacts roller chassis 236. Those of skill in the art will appreciate that one or both levers 218, 220 may include a flat outer surface 240, which allows the device to be marked with a logo or contact information of the patient's hospital, physician, or clinic.

Top and bottom clamshells 214, 216 may advantageously each be integrally formed by injection molding. Any suitable material, or combination of materials, can be selected for forming the various components of the apparatus of the present invention. Those of skill in the art will appreciate that materials are selected to have durability and rigidity sufficient for a desired application of the device and many plastic materials will meet these criteria. Also, for many medical applications, materials that are sterilizable, such as by gamma radiation, are also desirable.

First and second levers 218, 220 are also each integrally formed, for example, by injection molding. The side outer surface 242 of each lever 218, 220 may be concave which allows a user to easily and ergonomically hold the device 210 in either the left or right hand.

Roller chassis 236 includes plate 248, which divides the roller chassis 226 into top and bottom compartments 244, 246. Roller chassis 236 includes sliding mechanism 235 thereon that is slidingly coupled to top clamshell 214 on an underside thereof. Sliding mechanism 235 allows roller chassis 236 to slide into channel 268 when an opposing force is applied to spring 245. Plate 248 includes an aperture 250 thereon for receiving a shoulder screw 239 for rotatably coupling roller 238 to roller chassis 236 in first compartment 244. Those of skill in the art will appreciate that any mechanism for rotatably coupling roller 238 to roller chassis 236 may be utilized. Those of skill in the art will also appreciate that roller chassis 236 may also be stationary in which case it would simply be positioned further into passageway 268. Roller 238 includes top and bottom lips 237, 238 that act to maintain surgical drain tube 262 in position so that it does not slip out of roller 238 in operation. However, those of skill in the art will appreciate that lips 237, 238 are not necessary as guide 262 will maintain tube 78 in place. Roller chassis 236 also includes drain guide 262 operably coupled to the top compartment 244. Drain guide 262 has a rounded portion 264 that, in operation, projects through housing opening 266 and into drain channel 268 positioned in housing 212. Drain guide 262 overlaps drain channel 268 and functions to further hold tubular drain 78 in position between top and bottom lips 237, 238 of roller 238. Drain guide 262 may be constructed from silicone or rubber and the like. Those of skill in the art will appreciate that while a number of different materials may be used, drain guide 262 is ideally pliable to allow for easy insertion of flexible drain tubing 78 into channel 268. Drain guide 262 may also be formed as part of housing 212 as disclosed above with respect to the embodiments of FIGS. 1-6 or still alternatively include two drain guides on housing 212).

Figure 12:
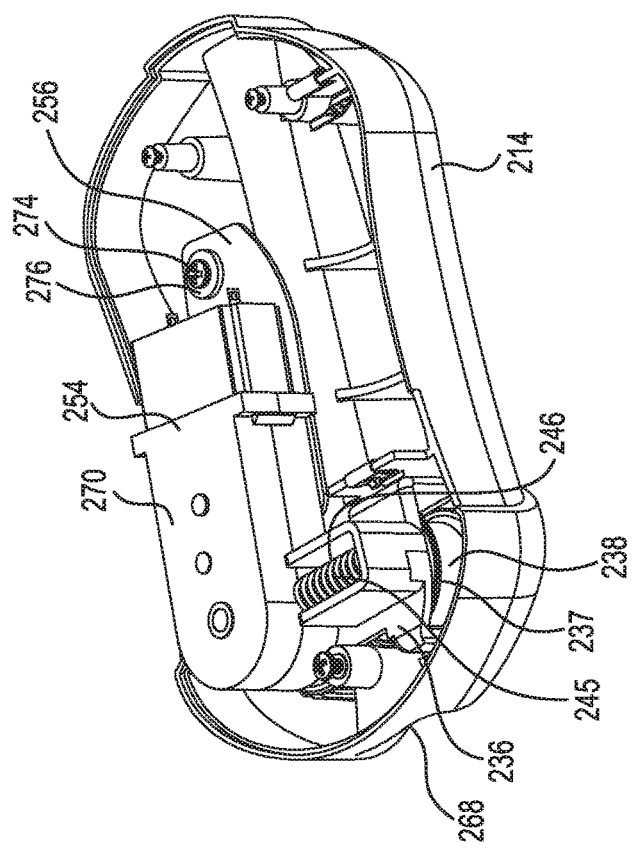
FIG. 12 illustrates the bottom side of the components parts of the device of FIG. 7 viewed as positioned in the top clamshell.
Figure 13:
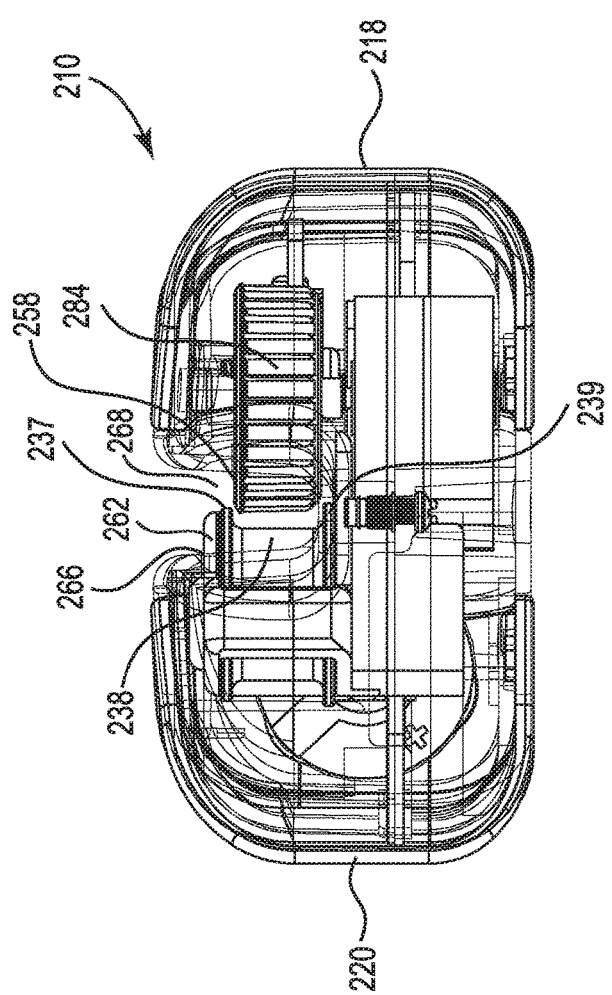
FIG. 13 is a front view showing the relationship of the two rollers.

Bottom compartment 248 of roller chassis 236 may be rectangular or cylindrically shaped and receives compression spring 245 therewithin. Compression spring 245 biases drive mechanism 252 away from roller 238 and roller chassis 236, as best seen in FIG. 12, in the "normal" or "disengaged" position in which the surgical drain tubing is not engaged. Those of skill in the art will appreciate that while a compression spring 245 is depicted, other types of biasing means, such as leaf springs and the like, may be substituted. In the "normal" or "disengaged position, roller chassis 236, roller 238 and guide 262 project slightly into channel 268.

Drive mechanism 252 broadly includes gear motor (not shown) housed within gear motor housing 270, retaining plate 256, drive roller 258, battery pack 260 and switch 288. Switch includes actuation button 289 which is in contact with, and actuated by, third projection 230 on lever 218. Retaining plate 256 is pivotally coupled at a first end thereof to pivot point 278 by fastener 276. Retaining plate 256 is coupled at a second end to gear motor housing 270. Drive roller 258 is rotatably coupled to gear motor 254 via drive shaft 286. Optionally drive roller 258 may include teeth 284 circumferentially surrounding drive roller 258 to assist in gripping drain tubing 78 as drain tubing 78 moves through channel 268. Battery pack 260 is electrically coupled to gear motor 254 via wires (not shown) and houses one or more batteries 290.

Figure 8:
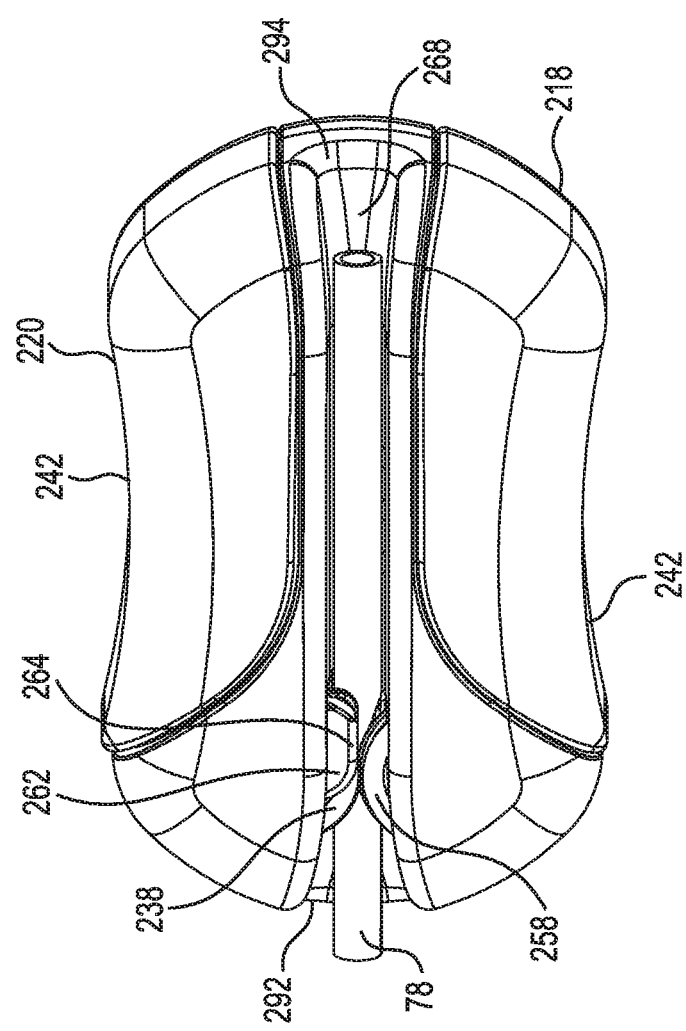
FIG. 8 is a top view of the device of FIG. 7 with surgical drain tubing inserted into channel and between rollers.
Figure 9:
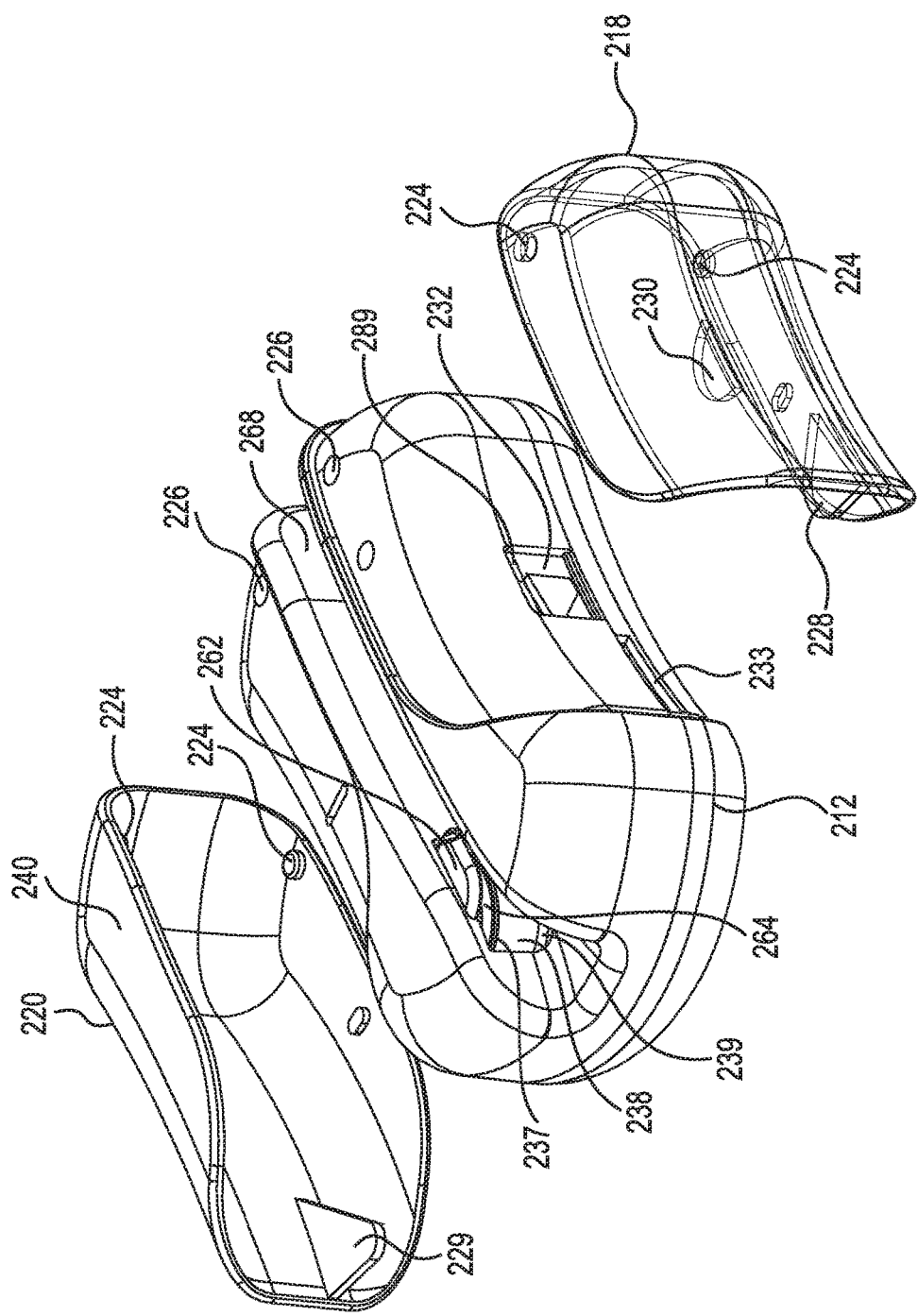
FIG. 9 is a perspective view of the device of FIG. 7 showing two side levers exploded away from the main body with the first lever being transparent to show projections.
Figure 10:
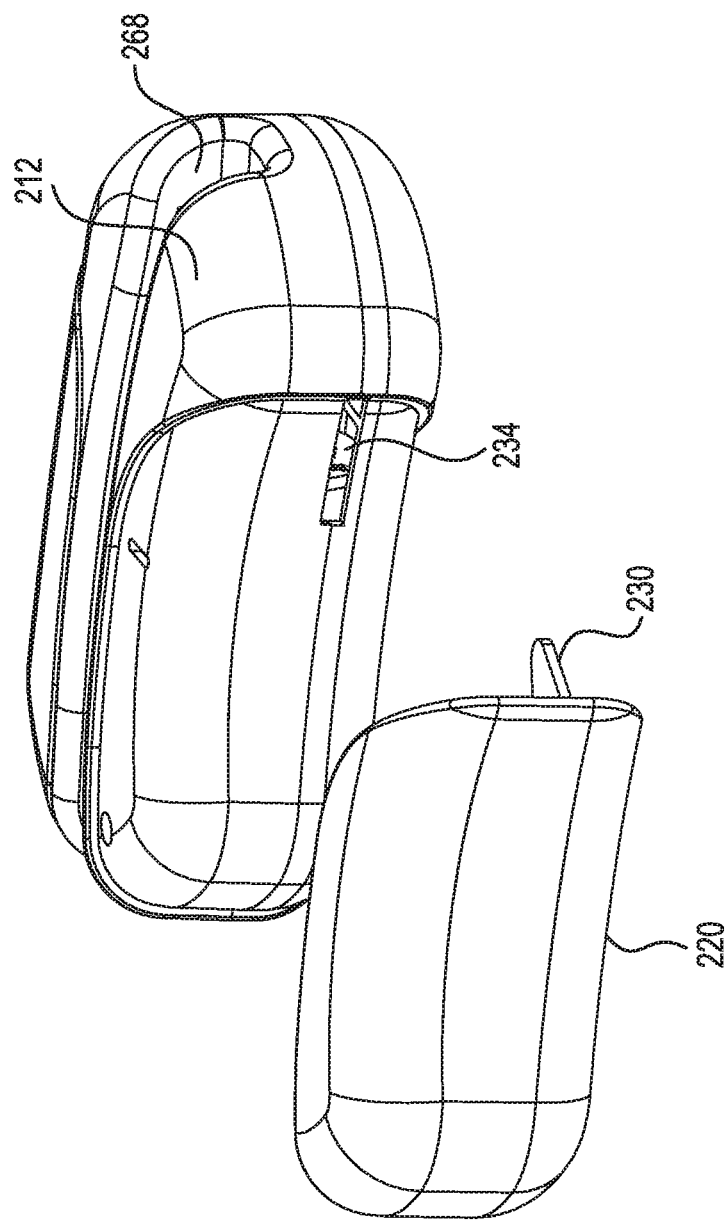
FIG. 10 is a side view of the device of FIG. 7 showing second lever exploded away from housing.
Figure 11:
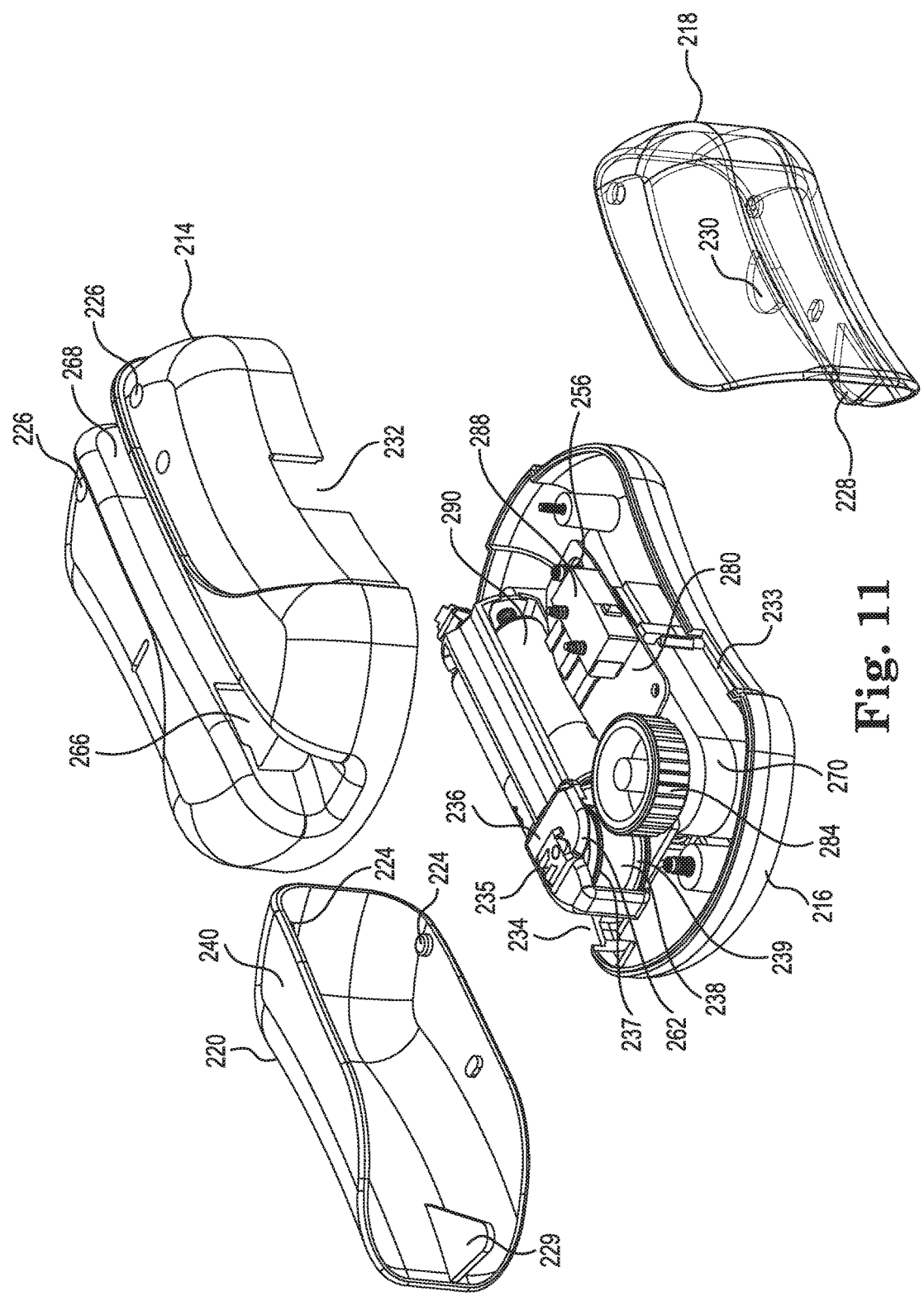
FIG. 11 is a partially exploded view showing the component parts of the device of FIG. 7 positioned in the bottom clamshell.

Top clamshell 214 includes an integrally molded channel 268 which accommodates surgical drain tubing 78 therein during operation, as best seen in FIG. 8. The distal and proximal ends of 292, 294 of drain channel 268 may be fan-shaped or flared and thus have a width that is greater than the width of drain channel 268 in the center. This allows the surgical drain tubing 78 (or feeding tube) to be easily inserted and removed from drain channel 268 as well as facilitate movement of the tube 78 through the device 210 when tubing enters or exits the device at multiple angles. Other shapes may be used and fall within the scope of the invention. Those of skill in the art will also appreciate that the width of the passageway may be varied depending on the outer diameter of the surgical drain or feeding tube tubing to be inserted therein. However, for economies in the manufacturing process drain channel 268 should be sufficiently wide to accommodate most diameters of tubing, such as 15, 19, 20, 22 and/or 24 French surgical drains or slightly larger feeding tubes.

In operation, a user places surgical tubing 78 in channel 268 under the pliable tube guide 262 and between lips 237, 239 of roller 238. Those of skill in the art will appreciate that lips 237, 239 may be eliminated and tube guide 262 would be sufficient to hold tubing 78 in channel 268. The user then squeezes levers 218, 220 inwardly toward housing 212. Third projection 230 triggers motor activation button 289 which actuates or energizes actuator 254. Many different types of actuators may be used including, but not limited to, gear motors, rotary solenoids, electromechanical rotary devices, and electromagnetic rotary devices. As an exemplary embodiment, actuator 254 is disclosed herein as a gear motor housed within gear housing 270, which houses gears that rotate drive roller 258. When gear motor is actuated, the drive shaft 286 coupled to drive roller 258 causes drive roller 258 to rotatably move. At the same time, when levers 218, 220 are squeezed inwardly toward housing 212, first projection 228 pushes against the gear housing 270 and overcomes the force being applied by compression spring 245 causing drive mechanism 252 to pivot at pivot point 274 such that drive roller 258 moves into channel 268 and rotatably engages surgical drain tube 78. On the opposite side and simultaneously, second projection 229 exerts a force against roller chassis to overcome the force of compression spring 245 causing roller chassis to slide such that roller 238 causes surgical drain 78 to firmly engage teeth 284 of drive roller 258. Although the motorized drive roller 258 is designed to cause the drain tubing 78 to move through the channel 268 to clear the drain tubing 78 of its contents, the user may also guide the device 210 down the length of the tubing. When the user releases the levers 218, 220 the motor becomes de-energized and drive roller 258 cease to rotate. Releasing levers 218, 220 also releases force on compression spring causing the drive mechanism 252 to pivot back to its original "disengaged" position and also causes roller chassis to slide back to its original position.

Figure 14:
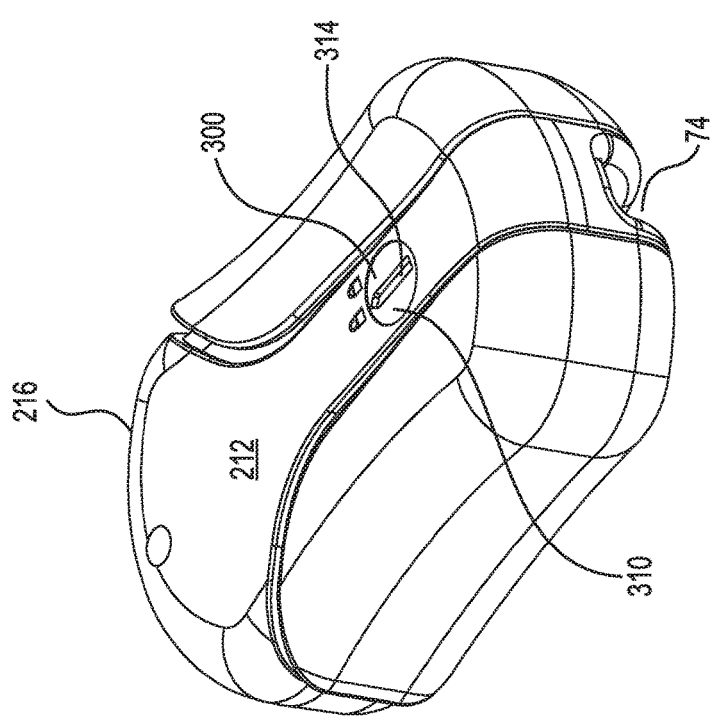
FIG. 14 is a perspective view of the bottom side of bottom clam shell depicting a mechanical locking mechanism thereon.
Figure 15:
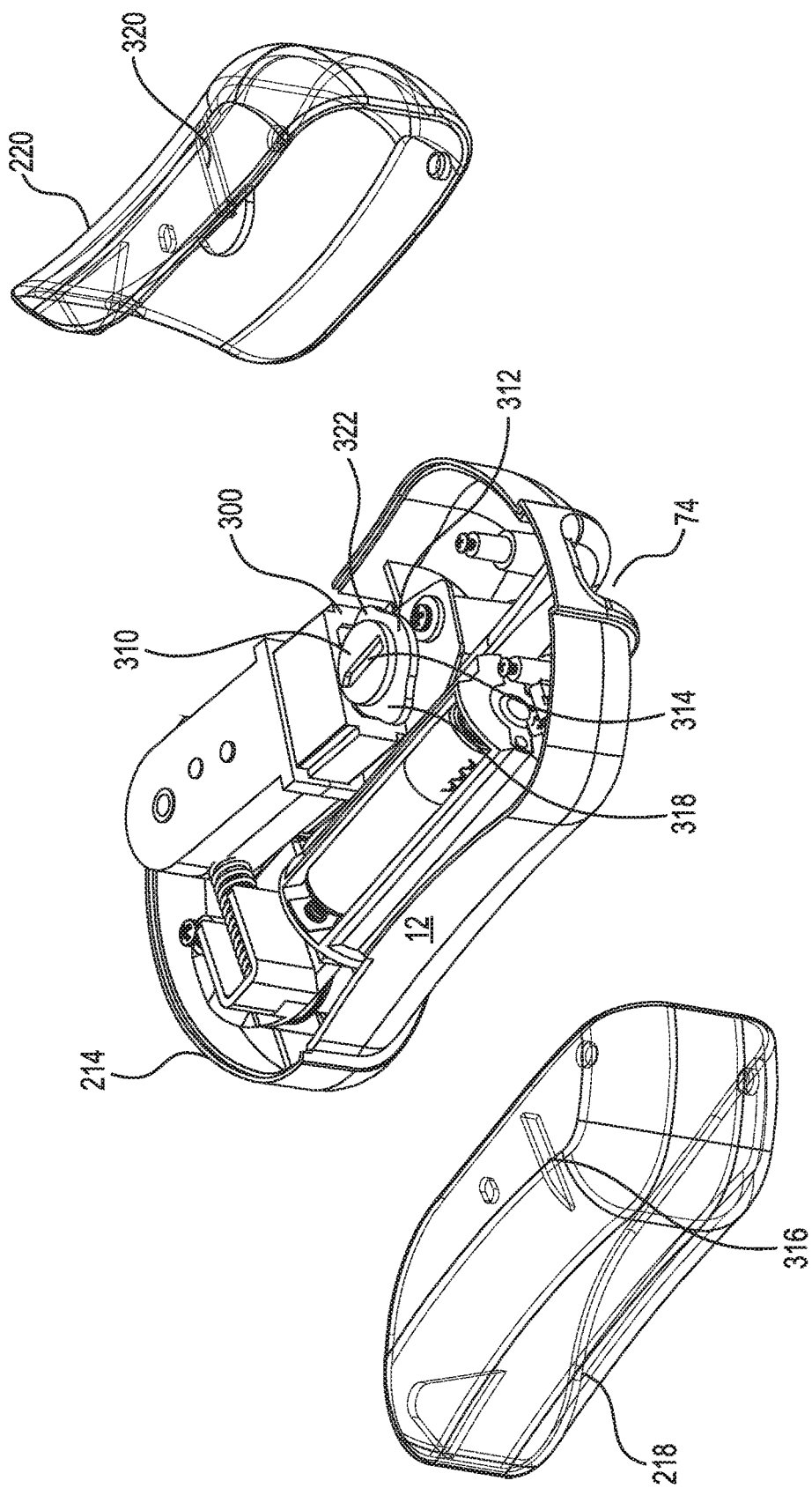
FIG. 15 is a perspective view of the top clamshell, inverted to show placement of the mechanical locking mechanism and arms that contact mechanical locking mechanism projecting from levers.

Referring now to FIGS. 14 and 15 optional mechanical locking mechanism 300 is shown. Like elements are labeled with like reference numerals. Mechanical locking mechanism broadly includes disk 310 rotatably coupled to rotatable cam 312. Disk 310 is positioned through bottom clamshell 216 to rotatably couple to rotatable cam 312. Disk 310 includes a slot 314 thereon that receives a tool, such as a screwdriver, that mechanically rotates disk 310. Those of skill in the art will appreciate that slot 314 may also be configured to accommodate cruciform types of tools such as Phillips, Frearson, Mortorq and the like, hex types of tools, thumbscrews and combination drives. Levers 218, 220 each include arms 316, 320 integrally molded thereto or otherwise fixedly coupled to the underside. In the locked position arms 316, 320 abut projecting portions 318, 322, respectively, of rotatable cam 312. When arms 316, 320 abut projecting portion 318, 322 they prevent a user from depressing levers 218, 220. When disk 310 is rotated to the open position, arms 316, 320 no longer abut projecting portions 318, 322 of cam 312 and levers 218, 220 may be depressed to actuate actuator.

Other aspects of the invention may include the drain cleaner as a kit including a measuring cup for the patient to measure fluid output, a log book for recording fluid output and a carrying pouch for storing the drain cleaner for ease of mobility.

Although the present invention has been described with reference to certain aspects and embodiments, those of ordinary skill in the art will appreciate that changes may be made in form and detail without departing from the spirit and scope of the invention.

What is claimed is:

1. A device for moving contents of a tube by acting on an exterior of the tube comprising: a housing including a top portion and a bottom portion, the top portion including a tube passageway extending along a length thereof for holding a tube therein; a roller chassis moveable between a first position and a second position and coupled to the housing; a first roller for contacting the tube, the first roller housed within the roller chassis and moveable between a first position in which the tube is disengaged and a second position in which the tube is engaged; a second roller rotatably coupled to an actuator for rotatably energizing the second roller, the second roller moveable between a first position in which the tube is disengaged and a second position in which the tube is engaged, the first roller and the second roller configured to matingly compress the tube; biasing means for biasing the first roller and the second roller in opposite directions; and at least a first lever operably coupled to the housing, the first lever configured to actuate the actuator and move the second roller to the second position.

2. The device of claim 1 further comprising a second lever, the second lever including a projection on an interior surface thereof receivable in the housing, the projection configured to engage the roller chassis to cause the second roller to slidably move between the first position in which the tube is disengaged and the second position in which the tube is engaged.

3. The device of claim 1 wherein the actuator includes a gear motor rotatably coupled to the second roller.

4. The device of claim 1 wherein the actuator is coupled to a pivot plate pivotally moveable between first and second pivot positions.

5. The device of claim 1 wherein the biasing means comprises a compression spring.

6. The device of claim 1 wherein the biasing means is received within a compartment of the roller chassis.

7. The device of claim 1 wherein the second roller includes a plurality of teeth circumferentially disposed thereabout.

8. The device of claim 1 wherein the actuator is selected from a gear motor, a rotary solenoid, electromechanical rotary device and electromagnetic rotary device.

9. The device of claim 1 wherein the at least first lever includes first and second projections thereon receivable within first and second openings in the housing, respectively, the first projection configured to actuate a motor activation switch and the second projection for pivotally moving the first roller between a first pivot position in which the tube is disengaged and a second pivot position in which the tube is engaged.

10. The device of claim 1 wherein the roller chassis is slidably coupled to the housing and slidably moveable between the first position and the second position.

11. The device of claim 1 wherein the roller chassis includes a first compartment for housing the first roller and a second compartment for housing biasing means.

12. The device of claim 1 wherein said second roller is pivotally moveable between a first pivot position in which the tube is disengaged and a second pivot position in which the tube is engaged.

13. The device of claim 1 wherein the actuator is rotatably energizable by one or more batteries.

14. The device of claim 1 further comprising a mechanical locking mechanism including a rotatable disk positioned on an outside of the housing and rotatably coupled to a rotatable cam operably coupled within said bottom portion and including two projecting portions.

15. The device of claim 14 wherein said at least one lever comprises two levers each of which includes a locking arm thereon, each of the locking arms configured to abut the two projecting portions to lock each of the two levers in a disengaged position.

16. The device of claim 1 wherein the second roller includes one or more convex projections and the first roller includes a concave channel that matingly receives the one or more convex projections.

17. The device of claim 16 wherein said convex projections comprise teeth.

18. The device of claim 1 wherein the top portion and the bottom portion are removably fastened to one another by fastening means selected from screws, adhesive, snap-fit and threads.

19. The device of claim 1 further comprising a drain guide that, in operation, is positioned in the tube passageway to maintain the tube in positon.

20. The device of claim 1 wherein the biasing means is a leaf spring.

21. The device of claim 1 wherein the biasing means is a compression spring.

22. The device of claim 1 wherein the first and second rollers are configured to matingly compress the tubing by a pre-determined amount.

* * * * *